US011844620B2

(12) United States Patent
Volpe et al.

(10) Patent No.: US 11,844,620 B2
(45) Date of Patent: Dec. 19, 2023

(54) CONFIGURING A CARDIAC MONITORING DEVICE

(71) Applicant: ZOLL Medical Corporation, Chelmsford, MA (US)

(72) Inventors: Shane S Volpe, Saltsburg, PA (US); Joshua Van Der Lee, Mars, PA (US); Gary A Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 213 days.

(21) Appl. No.: 17/247,918

(22) Filed: Dec. 30, 2020

(65) Prior Publication Data

US 2021/0113138 A1    Apr. 22, 2021

Related U.S. Application Data

(62) Division of application No. 15/445,447, filed on Feb. 28, 2017, now Pat. No. 10,912,478.

(51) Int. Cl.
*A61B 5/36*   (2021.01)
*A61B 5/363*  (2021.01)
(Continued)

(52) U.S. Cl.
CPC ............ *A61B 5/363* (2021.01); *A61B 5/0006* (2013.01); *A61B 5/335* (2021.01); *A61B 5/0205* (2013.01);
(Continued)

(58) Field of Classification Search
CPC ....... A61B 5/0464; A61B 5/0006; A61B 5/11; A61B 5/14551; A61B 5/14532; A61B 5/0205; A61B 5/4836; A61B 5/04325; A61B 5/0507; A61B 5/746; A61N 1/362; A61N 1/39; A61N 1/3904; A61N 1/046; A61N 1/0484
See application file for complete search history.

(56) References Cited

U.S. PATENT DOCUMENTS 6,253,099 B1     6/2001 Oskin et al.
2005/0131480 A1*  6/2005 Kramer ................ A61N 1/3627
                                                  607/30
(Continued)

*Primary Examiner* — Rex R Holmes
(74) *Attorney, Agent, or Firm* — FINCH & MALONEY PLLC

(57) ABSTRACT

A system for configuring an ambulatory medical device includes an ambulatory medical device configured to monitor at least one electrocardiogram signal received from a patient for an occurrence of one or more cardiac events. The system also includes a remote computing device configured to receive a set of threshold values related to operation of the ambulatory medical device. The threshold values identify one or more conditions indicative of an occurrence of one or more cardiac events. The remote computing device is configured to query a master lookup table to determine a lookup code associated with the received set of threshold values, establish a communication link with the ambulatory medical device, receive an activation notification indicating that the ambulatory medical device has been activated, and encode a key. The encoded key includes the lookup code. The remote computing device is configured to transmit the encoded key to the ambulatory medical device.

24 Claims, 10 Drawing Sheets

(51) Int. Cl.

| | |
|---|---|
| *A61B 5/00* | (2006.01) |
| *A61B 5/335* | (2021.01) |
| *A61N 1/39* | (2006.01) |
| *A61N 1/362* | (2006.01) |
| *A61B 5/0205* | (2006.01) |
| *A61B 5/145* | (2006.01) |
| *A61B 5/1455* | (2006.01) |
| *A61B 5/11* | (2006.01) |
| *A61B 5/0507* | (2021.01) |
| *A61N 1/04* | (2006.01) |

(52) U.S. Cl.
CPC ............... *A61B 5/0507* (2013.01); *A61B 5/11* (2013.01); *A61B 5/14532* (2013.01); *A61B 5/14551* (2013.01); *A61B 5/4836* (2013.01); *A61B 5/746* (2013.01); *A61N 1/046* (2013.01); *A61N 1/0484* (2013.01); *A61N 1/362* (2013.01); *A61N 1/39* (2013.01); *A61N 1/3904* (2017.08)

(56) References Cited

U.S. PATENT DOCUMENTS

| | | | |
|---|---|---|---|
| 2006/0281980 A1 | 12/2006 | Randlov et al. | |
| 2011/0270112 A1* | 11/2011 | Manera | A61B 5/332 |
| | | | 600/523 |
| 2013/0325078 A1* | 12/2013 | Whiting | A61N 1/3925 |
| | | | 607/7 |
| 2016/0078183 A1 | 3/2016 | Trygstad et al. | |

\* cited by examiner

| Heartrate | | 150 | 155 | 160 | 165 | 170 | 175 | 180 | 185 | 190 | 195 | 200 |
|---|---|---|---|---|---|---|---|---|---|---|---|---|
| | Identifier | 1 | 2 | 3 | 4 | 5 | 6 | 7 | 8 | 9 | 10 | 11 |
| 20 | 1 | | | | | | | | | | | |
| 22 | 2 | | | | | | | | | | | |
| 24 | 3 | | | | | | | | | | | |
| 26 | 4 | | | | | | | | | | | |
| 28 | 5 | | | | | | x | | | | | |
| 30 | 6 | | | | | | | | | | | |
| 32 | 7 | | | | | | | | | | | |
| 34 | 8 | | | | | | | | | | | |
| 36 | 9 | | | | | | | | | | | |
| 38 | 10 | | | | | | | | | | | |
| 40 | 11 | | | | | | | | | | | |

| Identifier | 1 | 2 | 3 | 4 | 5 | 6 | 7 | 8 | 9 | 10 | 11 |
|---|---|---|---|---|---|---|---|---|---|---|---|
| 1 | 150, 20 | 155, 20 | 160, 20 | 165, 20 | 170, 20 | 175, 20 | 180, 20 | 185, 20 | 190, 20 | 195, 20 | 200, 20 |
| 2 | 150, 22 | 155, 22 | 160, 22 | 165, 22 | 170, 22 | 175, 22 | 180, 22 | 185, 22 | 190, 22 | 195, 22 | 200, 22 |
| 3 | 150, 24 | 155, 24 | 160, 24 | 165, 24 | 170, 24 | 175, 24 | 180, 24 | 185, 24 | 190, 24 | 195, 24 | 200, 24 |
| 4 | 150, 26 | 155, 26 | 160, 26 | 165, 26 | 170, 26 | 175, 26 | 180, 26 | 185, 26 | 190, 26 | 195, 26 | 200, 26 |
| 5 | 150, 28 | 155, 28 | 160, 28 | 165, 28 | 170, 28 | 175, 28 | 180, 28 | 185, 28 | 190, 28 | 195, 28 | 200, 28 |
| 6 | 150, 30 | 155, 30 | 160, 30 | 165, 30 | 170, 30 | 175, 30 | 180, 30 | 185, 30 | 190, 30 | 195, 30 | 200, 30 |
| 7 | 150, 32 | 155, 32 | 160, 32 | 165, 32 | 170, 32 | 175, 32 | 180, 32 | 185, 32 | 190, 32 | 195, 32 | 200, 32 |
| 8 | 150, 34 | 155, 34 | 160, 34 | 165, 34 | 170, 34 | 175, 34 | 180, 34 | 185, 34 | 190, 34 | 195, 34 | 200, 34 |
| 9 | 150, 36 | 155, 36 | 160, 36 | 165, 36 | 170, 36 | 175, 36 | 180, 36 | 185, 36 | 190, 36 | 195, 36 | 200, 36 |
| 10 | 150, 38 | 155, 38 | 160, 38 | 165, 38 | 170, 38 | 175, 38 | 180, 38 | 185, 38 | 190, 38 | 195, 38 | 200, 38 |
| 11 | 150, 40 | 155, 40 | 160, 40 | 165, 40 | 170, 40 | 175, 40 | 180, 40 | 185, 40 | 190, 40 | 195, 40 | 200, 40 |

CONFIGURING A CARDIAC MONITORING DEVICE

CROSS REFERENCE TO RELATED APPLICATIONS

This application is a divisional from U.S. patent application Ser. No. 15/445,447, filed Feb. 28, 2017, now U.S. Pat. No. 10,912,478, entitled "Configuring a Cardiac Monitoring Device," the disclosure of which is hereby incorporated by reference in its entirety.

BACKGROUND

The present disclosure is directed to configuring a medical device, and more specifically to configuring a wearable medical device such as a cardiac monitoring device.

There are a wide variety of electronic and mechanical devices for monitoring and treating patients' medical conditions. In some examples, depending on the underlying medical condition being monitored or treated, medical devices such as cardiac monitors or defibrillators may be surgically implanted or externally connected to the patient. In some cases, physicians may use medical devices alone or in combination with drug therapies to treat conditions such as cardiac arrhythmias.

One of the deadliest cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus also available from ZOLL Medical Corporation.

SUMMARY

An ambulatory medical device configured to monitor at least one electrocardiogram (ECG) signal received from a patient is described herein. In certain implementations, the ambulatory medical device includes a memory device implemented by a computer readable medium and configured to store a lookup table including a plurality of sets of threshold values for one or more cardiac parameters based on the at least one ECG signal monitored by the ambulatory medical device, a communications module configured to establish an operable connection with a remote computing device, and a processor operably connected to the memory device and the communications module. In some examples, the processor is configured to execute one or more computer-readable instructions to cause the processor to activate the ambulatory medical device upon initial power up of the ambulatory medical device, establish a communication link between the communications module and the remote computing device, receive an encoded key from the remote computing device, the encoded key based on a set of threshold values determined at the remote computing device, select a corresponding set of threshold values for the one or more cardiac parameters from the local lookup table based at least in part on the received encoded key from the remote computing device, and configure the ambulatory medical device to operate according to the set of threshold values selected from the local lookup table.

In certain implementations of the above ambulatory medical device, the processor is further configured to monitor the ECG signal for an occurrence of one or more cardiac events to determine whether one or more of the selected threshold values have been exceeded. In some examples, the one or more cardiac events include at least one of bradycardia and tachycardia. In some examples, the set of threshold values selected from the local lookup table includes at least one of an onset threshold for bradycardia and an onset threshold for tachycardia. In some examples, the processor is further configured to determine a heartrate for the patient based upon the at least one ECG signal.

In certain implementations of the above ambulatory medical device the processor is further configured to receive an updated lookup table from the remote computing device, and replace the local lookup table with the updated lookup table.

In certain implementations of the above ambulatory medical device the processor is further configured to receive a query from the remote computing device to verify the set of threshold values selected from the local lookup table, and transmit a response to the query, the response including the set of threshold values selected from the local lookup table.

In certain implementations of the above ambulatory medical device, the ambulatory medical device is configured to operate in both a therapeutic mode and a monitoring mode.

In certain implementations of the above ambulatory medical device, the ambulatory medical device includes at least one of a therapeutic medical device and a monitoring medical device. In some examples, the therapeutic medical device includes at least one of a portable defibrillator, a wearable defibrillator, a cardiac pacing device, a portable ventilator, a cardiopulmonary resuscitation system, and combinations thereof. In some examples, the monitoring medical device includes at least one of a mobile cardiac monitoring device, a patient weight monitor, a blood glucose monitor, a pulse oximeter, a blood pressure monitor, and a patient movement detector.

A system for configuring an ambulatory medical device is also described. The system includes an ambulatory medical device configured to monitor at least one ECG signal received from a patient for an occurrence of one or more cardiac events, and a first remote computing device. In some examples, the first remote computing device is configured to receive threshold values related to operation of the ambulatory medical device, the threshold values identifying one or more conditions indicative of an occurrence of one or more cardiac events, query a master lookup table to determine a lookup code associated with the received threshold values, establish a communication link with the ambulatory medical device, receive an activation notification indicating that the ambulatory medical device has been activated, encode a key, the encoded key including the lookup code, and transmit the encoded key to the ambulatory medical device.

In certain implementations of the above system, the ambulatory medical device is further configured to receive the encoded key from the remote computing device, select a corresponding set of threshold values for the one or more cardiac parameters from a local lookup table based at least in part on the received encoded key, and monitor the ECG signal for an occurrence of one or more cardiac events to determine whether one or more of the selected threshold values have been exceeded. In some examples, the ambulatory medical device includes a memory device implemented by a computer readable medium configured to store the local lookup table. In some examples, selecting a corresponding set of threshold values includes determining a location in the local lookup table from the encoded key, and determining the set of threshold values stored in the lookup table at the identified location. In some examples, the first remote computing device is further configured to query the ambulatory medical device to determine what set of threshold values the ambulatory medical device is operating according to, and confirm that the set of threshold values the ambulatory medical device is operating according to matches the received threshold values.

In certain implementations of the above system, the first remote computing device is further configured to store the master lookup table, wherein the master lookup table includes all possible combinations of the threshold values, and transmit a copy of the master lookup table to the ambulatory medical device as an updated lookup table. In some examples, the ambulatory medical device is configured to receive the updated lookup table, and replace the local lookup table with the updated lookup table.

In certain implementations of the above system the one or more cardiac events include at least one of bradycardia and tachycardia.

In certain implementations of the above system the ambulatory medical device is configured to operate in both a therapeutic mode and a monitoring mode.

In certain implementations of the above system the ambulatory medical device includes at least one of a therapeutic medical device and a monitoring medical device. In some examples, the therapeutic medical device includes at least one of a portable defibrillator, a wearable defibrillator, a cardiac pacing device, a portable ventilator, a cardiopulmonary resuscitation system, and combinations thereof. In some examples, the monitoring medical device includes at least one of a mobile cardiac monitoring device, a patient weight monitor, a blood glucose monitor, a pulse oximeter, a blood pressure monitor, and a patient movement detector.

A second ambulatory medical device configured to monitor at least one ECG signal received from a patient is also described. The second ambulatory medical device includes a memory device implemented by a computer readable medium and configured to store a local data structure including a plurality of threshold values for each of a plurality of cardiac parameters based on the at least one ECG signal monitored by the ambulatory medical device, a communications module configured to establish an operable connection with a remote computing device, and a processor operably connected to the memory device and the communications module. In some examples, the processor is configured to execute one or more computer-readable instructions to cause the processor to activate the ambulatory medical device upon initial power up of the ambulatory medical device, establish a communication link between the communications module and the remote computing device, receive an encoded key from the remote computing device, the encoded key based on a set of threshold values determined at the remote computing device, determine lookup information based upon the received encoded key from the remote computing device, wherein the lookup information comprises a location identifier for a threshold value for each of the plurality of cardiac parameters, select a set of threshold values for the plurality of cardiac parameters from the local data structure based at least in part on the lookup information, and configure the ambulatory medical device to operate according to the set of threshold values selected from the local data structure.

In certain implementations of the above second ambulatory medical device, the local data structure includes a three-dimensional data structure. In some examples, the lookup information includes a set of coordinates indicating a point within the three-dimensional data structure that corresponds to the selected set of threshold values.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 6 illustrates a sample master settings lookup table, in accordance with an example of the present disclosure.

FIG. 8 illustrates a sample local lookup table, in accordance with an example of the present disclosure.

DETAILED DESCRIPTION

Figure 1:
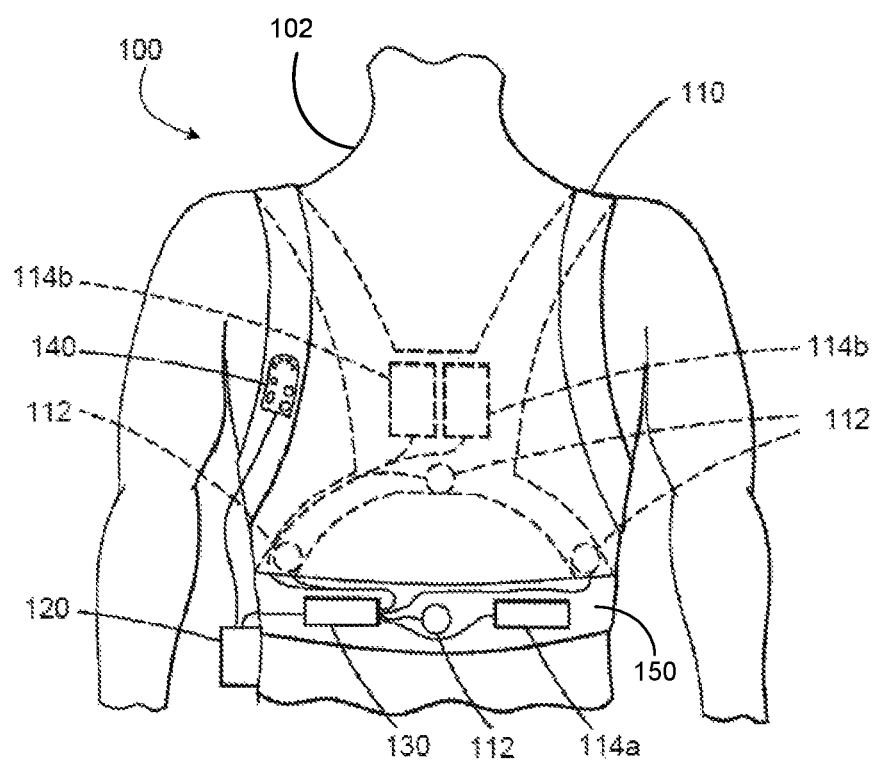
FIG. 1 depicts a wearable medical device, in accordance with an example of the present disclosure.

Wearable medical devices, such as cardiac monitoring devices, can be customized for a particular patient based upon a doctor's desired settings. For example, a doctor can set onset thresholds for various cardiac events such as Bradycardia and Tachycardia. However, existing methods of configuring these devices typically require entering a configurations mode on the device where the doctor (or another similar caregiver) can access individual settings such as, for example, Bradycardia and Tachycardia onset values, and modify those values per their desired settings. However, such a process is likely to cause confusion amongst different manufacturers' products (as they likely have different setup routines), and can be prone to error if the person programming the device enters an incorrect value for one or more settings. In other existing techniques, a new configuration file can be created for each wearable medical device being customized. However, such an approach requires transferring the configuration file to the wearable medical device via, for example, a wireless connection.

The present disclosure relates to an improved process for updating settings on a wearable medical device. The doctor can access an application or web-portal (e.g., an e-ordering application or a manufacturer specific web portal) and provide settings and threshold information for a particular patient such that a monitoring device can be configured for a specific patient. The settings and threshold information can be automatically encoded by, for example, a remote computing device such as a server maintained by a device manufacturer or distributor. The encoded information can be transmitted directly to the wearable medical device. The wearable medical device can decode the information and load the settings and threshold information according to one or more configuration processes such as those described in detail herein.

An improved process for updating settings on a wearable medical device as is described herein has several advantages. For example, a physician or other caregiver can access the same web-portal for multiple products that the physician prescribes. In such an example, the physician can learn to navigate a single interface regardless of the product being prescribed, thereby reducing the potential for incorrectly setting up a device when compared to on-device setup as described above, which can vary greatly between devices and manufacturers. Another advantage to the improved process as described herein is that minimal data is transmitted to the wearable medical device. Rather than sending a comparatively large file such as a configuration file as is done in existing techniques, the encoded settings and threshold information can be transferred to the wearable medical device as taught herein, thereby reducing the amount of data transferred, the bandwidth required for the data transfer, and the inherent monetary costs associated with data transfer.

In an example of an improved process for updating settings on a wearable medical device as is described herein, a patient can visit their physician for a routine cardiac examination. The physician can prescribe a cardiac monitoring device that the patient is to wear for a period of time (e.g., 30 days). Some cardiac monitoring devices can come with onset threshold values set to default values. However, for particular patients, the physician may want to alter the default settings. The physician can access an online configuration tool (e.g., through an e-ordering application or interface for the cardiac monitoring device manufacturer) and enter in a set of customized thresholds for the patient. This customized information can be received and processed by a remote computing device such as a remote server. The remote server can encode the threshold information as, for example, a key and, upon activation of the cardiac monitoring device, can transmit the encoded key to the cardiac monitoring device. The cardiac monitoring device can then decode the key, load the proper settings and threshold information, and operate according to the intended settings and thresholds as set by the physician.

Such an approach provides several advantages over the existing techniques. For example, the physician is not directly altering the settings on the cardiac monitoring device and, as such, is less likely to make an error or inadvertently change a setting or threshold they did not intend to adjust. Additionally, as the remote server can be configured to transmit the settings and threshold information as an encoded key (in certain implementations without any extraneous other configuration information), the amount of data transmitted to the cardiac monitoring device can be limited while still providing a high level of security.

Example Medical Devices

The teachings of the present disclosure can be generally applied to external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device can be capable of continuous use by the patient. In some implementations, the continuous use can be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., electrocardiogram (ECG) information, including arrhythmia information, heart sounds, etc.) and/or non-cardiac information (e.g., blood oxygen, the patient's temperature, glucose levels, tissue fluid levels, and/or lung sounds). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, lung sounds (e.g., using microphones and/or accelerometers), breath sounds, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In some implementations, the medical device may be a patient monitoring device with no treatment or therapy functions. For example, such a patient monitoring device can include a cardiac monitoring device or a cardiac monitor that is configured to monitor one or more cardiac physiological parameters of a patient, e.g., for remotely monitoring and/or diagnosing a condition of the patient. For example, such cardiac physiological parameters may include a patient's ECG information, heart sounds (e.g., using accelerometers or microphones), and other related cardiac information. A cardiac monitoring device is a portable device that the patient can carry around as he or she goes about their daily routine. The cardiac monitor may be configured to detect the patient's ECG through a plurality of cardiac sensing electrodes. For example, a cardiac monitor may be attached to a patient via at least three adhesive cardiac sensing electrodes disposed about the patient's torso. Such cardiac monitors are used in mobile cardiac telemetry (MCT) and/or continuous cardiac event monitoring applications, e.g., in patient populations reporting irregular cardiac symptoms and/or conditions. Example cardiac conditions can include atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., 10 to 30 days, or more. In some mobile cardiac telemetry applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, heart sounds (e.g., using accelerometers or microphones), lung sounds, breath sounds, sleep related parameters (e.g., snoring, sleep apnea), tissue fluids, among others.

Example Wearable Medical Devices

FIG. 1 illustrates an example medical device 100 that is external, ambulatory, and wearable by a patient 102, and configured to implement one or more configurations described herein. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes), one or more therapy electrodes 114a and 114b (collectively referred to herein as therapy electrodes 114), a medical device controller 120, a connection pod 130, a patient interface pod 140, a belt 150, or any combination of these. In some examples, at least some of the components of the medical device 100 can be configured to be affixed to the garment 110 (or in some examples, permanently integrated into the garment 110), which can be worn about the patient's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and at least one of the therapy electrodes 114 can be included on a single integrated patch and adhesively applied to the patient's body.

The sensing electrodes 112 can be configured to detect one or more cardiac signals. Examples of such signals include ECG signals and/or other sensed cardiac physiological signals from the patient. In certain implementations, the sensing electrodes 112 can include additional components such as accelerometers, acoustic signal detecting devices, and other measuring devices for recording additional parameters. For example, the sensing electrodes 112 can also be configured to detect other types of patient physiological parameters and acoustic signals, such as tissue fluid levels, heart sounds, lung sounds, respiration sounds, patient movement, etc. Example sensing electrodes 112 include a metal electrode with an oxide coating such as tantalum pentoxide electrodes, as described in, for example, U.S. Pat. No. 6,253,099 entitled "Cardiac Monitoring Electrode Apparatus and Method," the content of which is incorporated herein by reference.

In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the medical device controller 120. One or more of the therapy electrodes 114 can be configured to deliver one or more therapeutic defibrillating shocks to the body of the patient 102 when the medical device 100 determines that such treatment is warranted based on the signals detected by the sensing electrodes 112 and processed by the medical device controller 120. Example therapy electrodes 114 can include conductive metal electrodes such as stainless steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means of a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

WMD/WCD Controller Description

Figure 2:
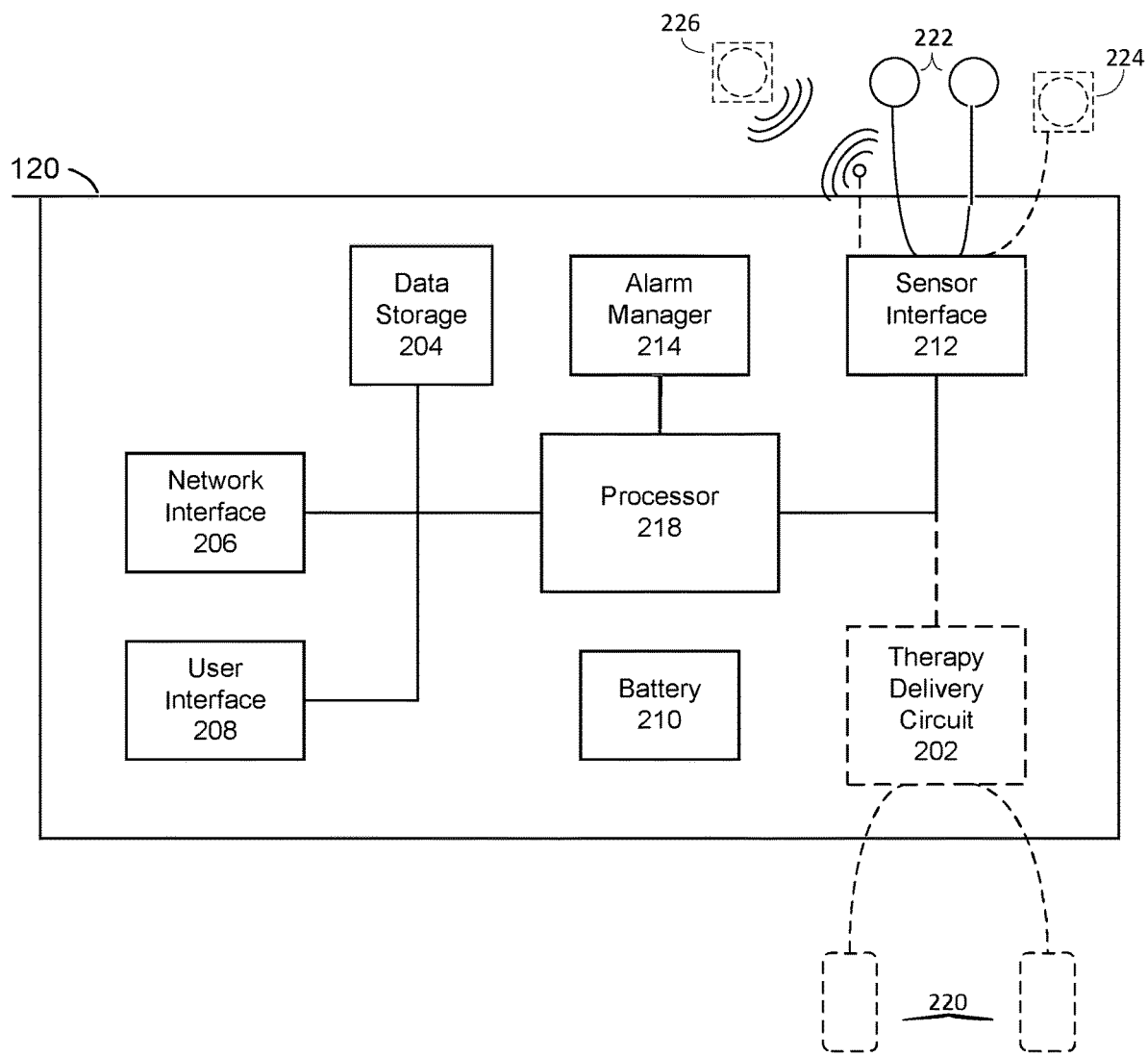
FIG. 2 depicts a schematic view of a sample controller for a wearable medical device such as that shown in FIG. 1, in accordance with an example of the present disclosure.

FIG. 2 illustrates a sample component-level view of the medical device controller 120. As shown in FIG. 2, the medical device controller 120 can include a therapy delivery circuit 202, a data storage 204, a network interface 206, a user interface 208, at least one battery 210, a sensor interface 212, an alarm manager 214, and least one processor 218. A patient monitoring medical device can include a medical device controller 120 that includes like components as those described above, but does not include the therapy delivery circuit 202 (shown in dotted lines).

The therapy delivery circuit 202 can be coupled to one or more electrodes 220 configured to provide therapy to the patient (e.g., therapy electrodes 114 as described above in connection with FIG. 1). For example, the therapy delivery circuit 202 can include, or be operably connected to, circuitry components that are configured to generate and provide the therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 218) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 uF can be used. The capacitors can have between 350 to 500 volt surge ratings and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuit 202 can be configured to perform the switching and pulse delivery operations, e.g., under control of the processor 218. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain implementations, the data storage can include executable instructions that, when executed, are configured to cause the processor 218 to perform one or more functions.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device.

In certain implementations, the user interface 208 can include one or more physical interface devices such as input devices, output devices, and combination input/output devices and a software stack configured to drive operation of the devices. These user interface elements may render visual, audio, and/or tactile content. Thus the user interface 208 may receive input or provide output, thereby enabling a user to interact with the medical device controller 120.

The medical device controller 120 can also include at least one battery 210 configured to provide power to one or more components integrated in the medical device controller 120. The battery 210 can include a rechargeable multi-cell battery pack. In one example implementation, the battery 210 can include three or more 2200 mAh lithium ion cells that provide electrical power to the other device components within the medical device controller 120. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can be coupled to one or more sensors configured to monitor one or more physiological parameters of the patient. As shown, the sensors may be coupled to the medical device controller 120 via a wired or wireless connection. The sensors can include one or more electrocardiogram (ECG) electrodes 222 (e.g., similar to sensing electrodes 112 as described above in connection with FIG. 1), heart sounds sensors 224, and tissue fluid monitors 226 (e.g., based on ultra-wide band radiofrequency devices).

The ECG electrodes 222 can monitor a patient's ECG information. For example, the ECG electrodes 222 can be galvanic (e.g., conductive) and/or capacitive electrodes configured to measure changes in a patient's electrophysiology to measure the patient's ECG information. The ECG electrodes 222 can transmit information descriptive of the ECG signals to the sensor interface 212 for subsequent analysis.

The heart sounds sensors 224 can detect a patient's heart sound information. For example, the heart sounds sensors 224 can be configured to detect heart sound values including any one or all of S1, S2, S3, and S4. From these heart sound values, certain heart sound metrics may be calculated, including any one or more of electromechanical activation time (EMAT), percentage of EMAT (% EMAT), systolic dysfunction index (SDI), and left ventricular systolic time (LVST). The heart sounds sensors 224 can include an acoustic sensor configured to detect sounds from a subject's cardiac system and provide an output signal responsive to the detected heart sounds. The heart sounds sensors 224 can also include a multi-channel accelerometer, for example, a three channel accelerometer configured to sense movement in each of three orthogonal axes such that patient movement/body position can be detected and correlated to detected heart sounds information. The heart sounds sensors 224 can transmit information descriptive of the heart sounds information to the sensor interface 212 for subsequent analysis.

The tissue fluid monitors 226 can use radio frequency (RF) based techniques to assess fluid levels and accumulation in a patient's body tissue. For example, the tissue fluid monitors 226 can be configured to measure fluid content in the lungs, typically for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 212 for subsequent analysis.

The sensor interface 212 can be coupled to any one or combination of sensing electrodes/other sensors to receive other patient data indicative of patient parameters. Once data from the sensors has been received by the sensor interface 212, the data can be directed by the processor 218 to an appropriate component within the medical device controller 120. For example, if heart data is collected by heart sounds sensor 224 and transmitted to the sensor interface 212, the sensor interface 212 can transmit the data to the processor 218 which, in turn, relays the data to a cardiac event detector. The cardiac event data can also be stored on the data storage 204.

In certain implementations, the alarm manager 214 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 214 can be implemented using hardware or a combination of hardware and software. For instance, in some examples, the alarm manager 214 can be implemented as a software component that is stored within the data storage 204 and executed by the processor 218. In this example, the instructions included in the alarm manager 214 can cause the processor 218 to configure alarm profiles and notify intended recipients using the alarm profiles. In other examples, alarm manager 214 can be an application-specific integrated circuit (ASIC) that is coupled to the processor 218 and configured to manage alarm profiles and notify intended recipients using alarms specified within the alarm profiles. Thus, examples of alarm manager 214 are not limited to a particular hardware or software implementation.

In some implementations, the processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to specific input stimulus in a specific way and generates a corresponding output based on that input stimulus. In some example cases, the processor 218 can proceed through a sequence of logical transitions in which various internal register states and/or other bit cell states internal or external to the processor 218 may be set to logic high or logic low. As referred to herein, the processor 218 can be configured to execute a function where software is stored in a data store coupled to the processor 218, the software being configured to cause the processor 218 to proceed through a sequence of various logic decisions that result in the function being executed. The various components that are described herein as being executable by the processor 218 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor or a 64-bit ARM processor. The processor can execute an embedded operating system, and include services provided by the operating system that can be used for file system manipulation, display & audio generation, basic networking, firewalling, data encryption and communications.

Example Monitoring Medical Device

Figure 3:
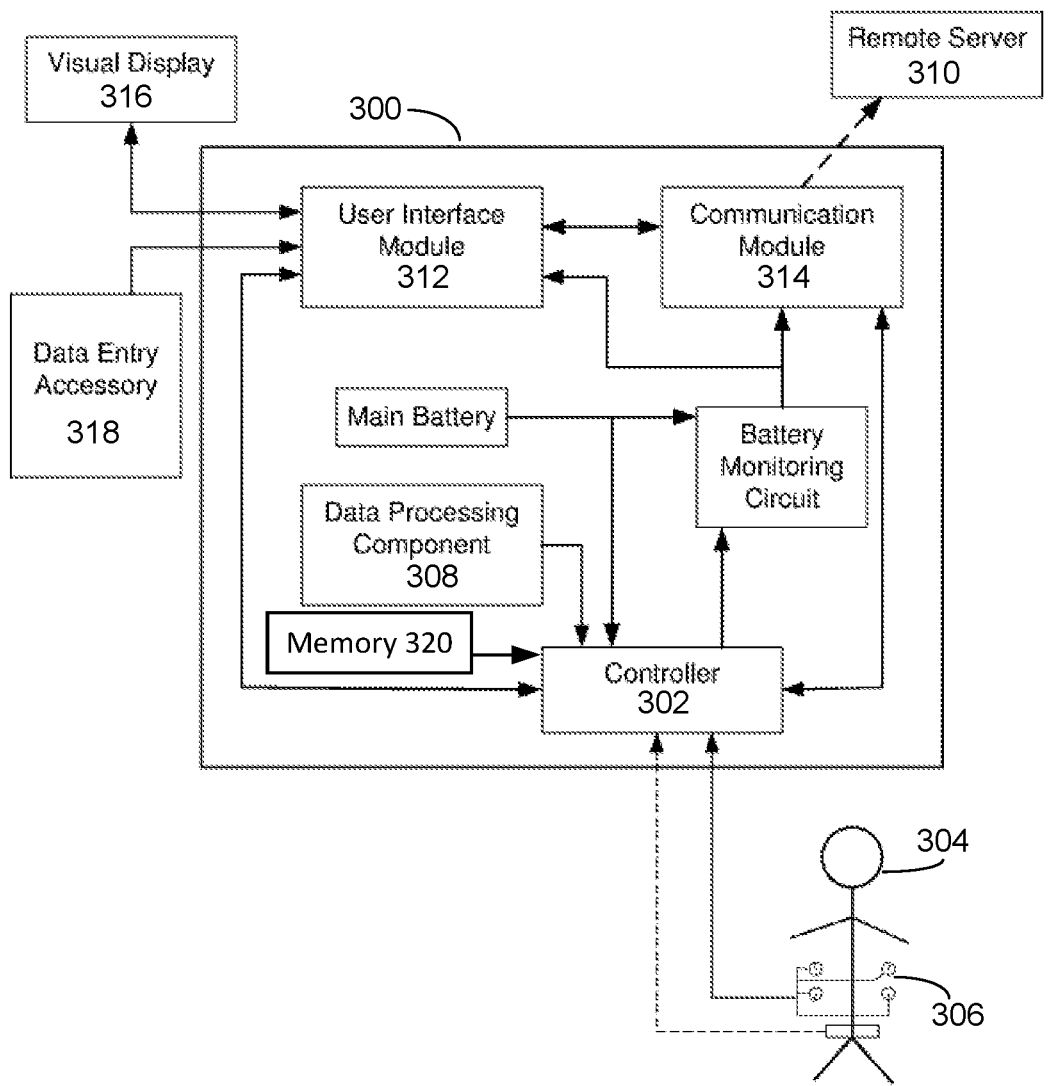
FIG. 3 depicts a schematic view of a sample mobile cardiac telemetry system as worn by a patient, in accordance with an example of the present disclosure.

With reference to FIG. 3, a detailed view of a sample cardiac monitoring medical device, for example, MCT device monitor 300, is illustrated. The monitor 300 can include a controller 302 that is communicatively coupled (e.g., wired or wirelessly coupled) to receive from sensors and/or electrodes 306 appropriately positioned on patient 304 signals (e.g., ECG data and/or heart sounds data from an acoustic sensor) indicative of cardiac activity of patient 304. In some examples, the sensors and/or electrodes can be an integral part of the housing structure of the patient monitor.

In some examples, the patient monitor 300 can be a cardiac monitor configured to receive cardiac data (e.g., ECG data and/or heart sounds data from an acoustic sensor). In some examples, the patient monitor 300 can, in addition to cardiac monitoring, perform monitoring of other relevant patient parameters, e.g., weight, glucose levels, blood oxygen levels, respiration rate, and blood pressure. The patient monitor 300 can also include a physiological data processing component 308 for collecting and conditioning the physiological data prior to storing the data locally at computer-readable storage media on the monitor 300 itself and/or transmitting the data to a remote server 310 or device.

In some examples, the patient monitor 300 can include motion sensors to track patient movement. In some examples, the patient monitor 300 can be a handheld device, such as a smartphone, a personal digital assistant, or a tablet device, comprising an application capable of receiving and/or processing patient data, either from internal sensors (e.g. motion sensors) or external sensors (e.g. wireless or wired sensors capable of sensing patient parameters, e.g. ECG, heart sounds, weight, glucose levels, blood oxygen levels, and blood pressure).

In some examples, the patient monitor 300 includes a user interface circuit or module 312 that allows the patient to perform one or more of the following activities: to control aspects of operation of the device, to manually enter patient information (e.g., patient name, age, gender), to manually enter information about a patient condition, and to initiate sending information to the remote server 310. The user interface module 312 can include a visual display 316 and a data entry accessory 318, such as buttons, trackballs, touchpads, and the like, for manually entering selections in response to a prompt from the user interface module 312. In other examples, the user interface module 312 can include a touch screen display for displaying information to the user and for receiving input (e.g., selections) from the user.

The patient monitor 300 can also include communication circuitry, referred to as communications circuit or module 314, for communicating with the remote server 310 (e.g., one or more computer systems) over a communications network. The patient monitor 300 can also communicate with other devices which may be a remote handheld device (e.g., a smartphone, a personal digital assistant, or a tablet device). In certain implementations, the communications module 314 can be configured to establish a communication link with the remote server 310 using a wide area data network such as a cellular data network. For example, the communications module 314 can include a 3G and/or 4G wireless transceiver configured to transmit and receive data over a 3G or 4G cellular network. It should be noted however, that 3G and 4G cellular data networks are provided by way of example only, and the communications module 314 can be configured to connect to various other types of communication networks to establish communication links with remote devices such as remote server 310.

In some examples, the patient monitor 300 can periodically (e.g., on a preset schedule) establish a wireless communication (e.g., cellular communication, Wi-Fi or Bluetooth) and send data, such as patient physiological information, to the server 310 over the network. For example, such physiological information can include, without limitation, patient symptom data (e.g., patient-reported symptoms and/or automatically detected patient information), related cardiac data including premature ventricular contraction (PVC) count, heart rate information, heart sounds data, ECG data (e.g., continuous ECG data), lung fluid measurements/data, patient thoracic impedance measurements/data, pectoral impedance measurements/data, blood pressure, temperature, blood glucose levels, and blood oxygen levels.

In other examples, the patient monitor 300 can be configured to aperiodically establish communication with the remote server 310 for the purpose of sending patient data. For example, the physiological data can be processed in accordance to a predetermined standard for transmission and can be transmitted in a secure HIPAA-compliant manner.

In other examples, the patient monitor 300 can be configured to send information to the remote server 310 when a transmission is initiated by the patient. For example, the patient can indicate that he or she is experiencing a symptom. As discussed hereinafter, the patient monitor 300 can be configured to send physiological information for the time period when the symptom was experienced to the remote server 310.

In some examples, the physiological data processing component 308 can be configured to analyze physiological information recorded by the monitor to identify when an event occurs. A non-limiting list of possible events that can be identified by analysis performed by the data processing component 308 of the patient monitor 300 includes: atrial fibrillation, bradycardia, tachycardia, atria-ventricular block, Lown-Ganong Levine syndrome, atrial flutter, sino-atrial node dysfunction, cerebral ischemia, syncope, atrial pause, and/or heart palpitations. The data processing component 308 can identify the event by performing an analysis algorithm, as is known in the art, for analyzing the patient physiological information. For example, to identify atrial fibrillation, the monitor 300 can be configured to analyze a measured ECG signal and determine an average QR interval for a plurality of preceding beats. The average QR interval or a change in the QR interval can be analyzed to identify atrial fibrillation events. Other analysis can be performed on an ECG signal to identify other events or conditions. In some examples, the events can be device-related events, such as when the device detects a battery-related condition, e.g., battery needs to be replaced, excessive noise, potential misidentification of one or more physiological parameters, or if one or more self-test features in the device fails or needs attention. When a physiological event or condition is identified, the patient monitor 300 can capture the physiological information related to the event, establish communication with the network, and send physiological information related to the event to the remote server. Similarly, when a device-related event or condition is identified, the patient monitor 300 can send diagnostic information relating to the event and/or condition. In some cases, where the device-related event relates to a noise event or a possible misidentification of physiological parameters, the patient monitor 300 can be configured to also send physiological information collected during the period of the device-related event for further analysis. Such types of transmission can be considered event based data transmission.

In another example, the patient monitor 300 can send all recorded physiological information to the remote server. The remote server 310 can manually or automatically perform the analysis for the events. For example, the patient monitor 300 can send data in batches at periodic intervals, such as once an hour or once a day, to the remote server 310 over the communications network.

In another example, the monitor 300 may continually communicate patient physiological information in substantially real-time to the remote server 310 whenever connectivity to the network is present. For example, continuous data transfer of physiological information can occur substantially in real-time, and may have brief device-induced delays, such as delays introduced through electronic switching. In some examples, the monitor 300 can communicate patient physiological information with a user-configurable delay between the time the information is recorded, and sent and/or delivered to the remote server.

In certain implementations, the monitor 300 can also include a memory 320. The memory 320 can be configured to store, for example, recorded ECG information and related data, as well as operational information such as configurations and settings information for the cardiac monitoring device. For example, the memory 320 can include a file that lists one or more monitoring thresholds indicative of onset conditions for various cardiac events such as Bradycardia and Tachycardia. Additionally, the memory 320 can include a local lookup table or set of lookup tables that include some or all potential combinations of possible threshold values for use when updating the configuration information associated with the cardiac monitoring device. The local lookup table, as well as processes for updating the cardiac monitoring device, are described in greater detail below.

Updating Wearable Medical Device Configuration Information

The present disclosure relates to an improved process for updating settings on a wearable medical device. In certain implementations, the wearable medical device can include one or more of a mobile cardiac monitoring device, a patient weight monitor, a blood glucose monitor, a pulse oximeter, a blood pressure monitor, and a patient movement detector. A physician can access an application or web-portal (e.g., an e-ordering application or a manufacturer specific web portal) and provide settings and threshold information for a particular patient such that a monitoring device can be configured for a specific patient. The settings and threshold information can be automatically encoded by, for example, a remote computing device such as a server maintained by a device manufacturer or distributor. The encoded information can be transmitted directly to the wearable medical device. The wearable medical device can decode the information and load the settings and threshold information according to one or more configuration processes such as those described in detail herein.

For example, a patient may visit their physician for a routine cardiac examination. The physician may prescribe a cardiac monitoring device that the patient is to wear for a period of time (e.g., 30 days). Some cardiac monitoring devices can come with onset threshold values set to default values. However, for particular patients, the physician may want to alter the default settings. The physician can access an online configuration tool (e.g., through an e-ordering application or interface for the cardiac monitoring device manufacturer) and enter in a set of customized thresholds for the patient. This customized information can be received and processed by a remote computing device such as a remote server. The remote server can encode the threshold information as, for example, a key and, upon activation of the cardiac monitoring device, can transmit the encoded key to the cardiac monitoring device. The cardiac monitoring device can then decode the key, load the proper settings and threshold information, and operate according to the intended settings and thresholds as set by the physician.

More specifically, in certain implementations, an ambulatory medical device is configured to monitor at least one electrocardiogram (ECG) signal received from a patient. The ambulatory medical device includes a memory device implemented by a computer readable medium configured to store a lookup table comprising a plurality of sets of threshold values for one or more cardiac parameters based on the at least one ECG signal monitored by the ambulatory medical device; a communications circuit or module configured to establish an operable connection with a remote computing device; and a processor operably connected to the memory device and the communications module. The processor can be configured to execute one or more computer-readable instructions to cause the processor to activate the ambulatory medical device upon initial power up of the ambulatory medical device, receive an encoded key from the remote computing device, the encoded key based on a set of threshold values determined at the remote computing device, select a corresponding set of threshold values for the one or more cardiac parameters from the local lookup table based at least in part on the received encoded key from the remote computing device, and configure the ambulatory medical device to operate according to the set of threshold values selected from the local lookup table.

In another implementation, a system for configuring an ambulatory medical device can include an ambulatory medical device configured to monitor at least one electrocardiogram (ECG) signal received from a patient for an occurrence of one or more cardiac events, and a first remote computing device operably connected to the ambulatory medical device. In some examples, the remote computing device can be configured to receive threshold values related to operation of the ambulatory medical device, the threshold values identifying one or more conditions indicative of an occurrence of one or more cardiac events, query a master lookup table to determine a lookup code associated with the received threshold values, receive an activation notification indicating that the ambulatory medical device has been activated, encode a key, the encoded key comprising the lookup code, and transmit the encoded key to the ambulatory medical device.

Remote Configuration of a Wearable Medical Device

As noted above, in certain implementations, a physician or other prescribing authority may want to change threshold and settings information on a wearable medical device being prescribed to a patient. For example, the physician can change onset threshold values for Bradycardia and Tachycardia on a patient by patient basis such that each patient's wearable medical device is specifically customized for them. It should be noted that, while the following examples are mainly directed to wearable cardiac monitoring devices (referred to herein as monitoring devices), the present disclosure is applicable to additional ambulatory and wearable medical devices including, but not limited to, wearable cardioverter defibrillators, cardiac pacing devices, portable ventilators, cardiopulmonary resuscitation systems, patient weight monitors, blood glucose monitors, pulse oximeters, blood pressure monitors, patient movement detectors, and combinations thereof.

Figure 4:
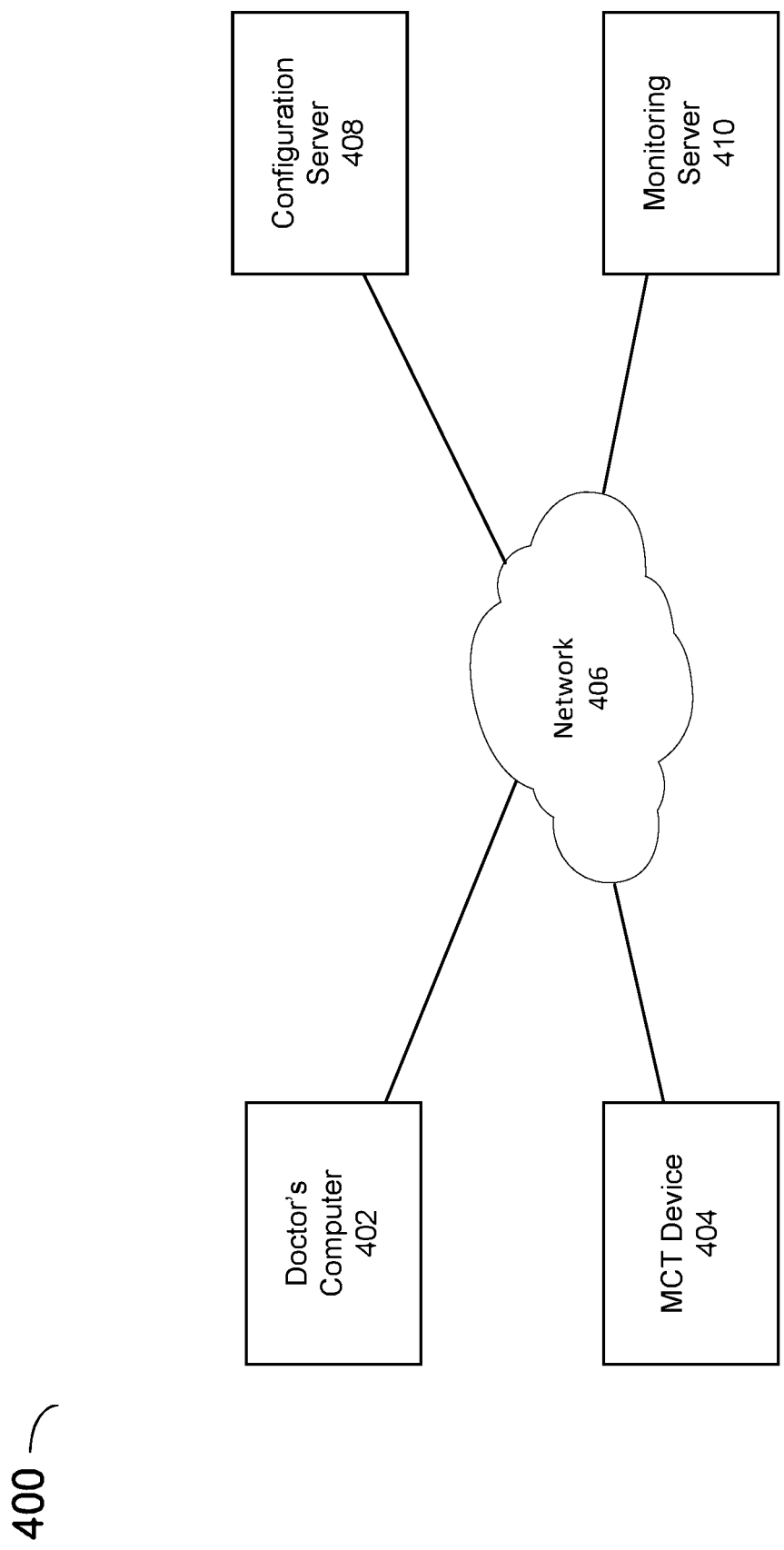
FIG. 4 illustrates a sample network topology, in accordance with an example of the present disclosure.

FIG. 4 illustrates a sample network 400 illustrating a sample topology showing how a physician can remotely access a remote computing device such as a configuration server during the initial prescription of a monitoring device to a patient. For example, a physician can access an e-ordering application or another similar online interface on their computer 402. The application can prompt the physician to alter or accept the default settings associated with the monitoring device 404. For example, the monitoring device 404 can be configured to monitor a patient's heartrate and identify one or more arrhythmia conditions. In certain implementations, the monitoring device 404 can be set with a default Bradycardia threshold of 30 bpm, and a default Tachycardia threshold of 150 bpm. For particular patients (e.g., patients with a history of heart disease), the physician might want to alter these default thresholds. For example, the physician might want the monitoring device 404 to identify a Tachycardia event at a lower heartrate (e.g., 160 bmp). As such, the physician can alter the threshold settings via the application on their computer 402, and transmit the updated threshold information to a remote server such as configuration server 408 via network 406. The configuration server 408 can process the threshold settings information and send data (e.g., as an encoded key as described below) to the monitoring device 404. Upon initialization, the monitoring device 404 can load the updated threshold information and begin monitoring the patient accordingly. In certain implementations, the monitoring device 404 can monitor the patient's heartrate for occurrences of cardiac events (e.g., arrhythmia events) using the updated threshold values.

Throughout the use of the device, the monitoring device 404 can collect and transmit patient information (e.g., ECG recordings) to a monitoring server 410. However, it should be noted that, in certain implementations, the configuration server 408 and the monitoring server 410 can be a single remote computing device maintained by, for example, a manufacturer of the cardiac monitoring devices.

Figure 5:
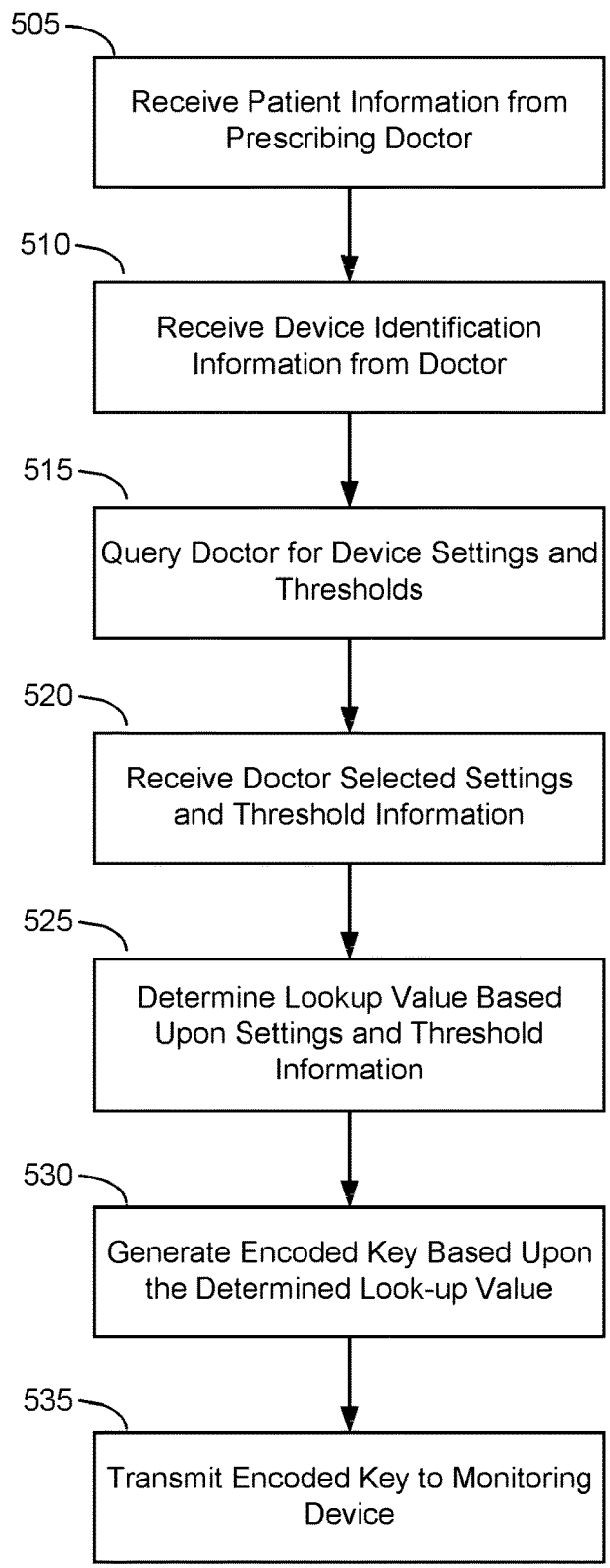
FIG. 5 illustrates a sample process flow for receiving device configuration information at a remote computing device, in accordance with an example of the present disclosure.

FIG. 5 illustrates a sample process as implemented by a remote configuration device such as configuration server 408 as described above in relation to FIG. 4. The configuration device can receive 505 patient information from the prescribing doctor. For example, when using an e-ordering application (as described above), the application can prompt or query the doctor for the patient information. For example, the application can prompt the doctor to provide various information such as patient name, patient identification number (e.g., health insurance policy number), demographic information, health history information, and other related information that is available to the doctor or included in the patient's medical record. The application can transmit the information to the configuration server.

The application can also prompt or query the doctor for information specific to the monitoring device being prescribed. For example, the application can query the doctor for various information such as device model information and serial number. The configuration server can receive 510 the device identification information and determine the device type being prescribed as well as the default settings for that device. The configuration server can then query 515 the doctor via the application for updated settings information. For example, the configuration server can determine, based upon the type of device being prescribed, what settings are customizable on the device. To continue the above example, the configuration server can determine that both the Bradycardia and Tachycardia onset threshold values are customizable. Thus, the configuration server can run a routine to identify the customizable settings and query the doctor for values for those settings via the application. In certain implementations, the application can automatically prepopulate entry fields (e.g., drop-down menus) with either the default values or with a doctor's preferred values.

Once the doctor has entered the customized threshold and settings information (or accepted the default values), the configuration server can receive 520 the doctor selected settings and threshold information. The configuration server can use the doctor setting and threshold information to identify a cell or other location in a data structure (e.g., master lookup table as described below in FIG. 6) that corresponds to the doctor selected setting and threshold information. The configuration server can use standard structure searching techniques such as SQL querying for databases to identify the database location. Based upon the identified location, the configuration server can determine 525 a database lookup value associated with the identified location. For example, a sample pseudo-code snippet for such a process can be:

```
Query Master Lookup Table (using received settings and threshold
information)
    Determine Lookup Value
    Return Coordinates (X, Y)
```

Based upon the determined lookup value, the configuration server can generate 530 an encoded key for transmission to the monitoring device. The encoded key can include an encoded character string that, when properly decoded, includes the lookup information for locating the identified location in the data structure. Based upon the identified location, the monitoring device can determine the settings and threshold information.

In certain implementations, a private/public key pair can be used to encode the key according to existing techniques. However, it should be noted that a private/public key pair is shown by way of example only and other encoding/encryption techniques can be used. For example, a sample pseudo-code snippet for using a private/public encryption scheme can be:

```
Generate Character String (using coordinate information)
Determine Monitoring Device Decryption Abilities (based upon device ID)
Encrypt String Based Upon Device Decryption Abilities
    Determine Encoding Scheme or Algorithm
    Create Cipher for Symmetric Key Encryption
    Create Key Generator
    Generate Session Key
    Initialize Symmetric Cipher Using Session Key
    Encrypt String with Symmetric Cipher
    Generate Asymmetric Cipher (from Public Key)
    Seal Session Key Using Asymmetric Cipher
```

After encoding the key (including the lookup information for the threshold and settings information), the configuration server can transmit 535 the encoded key to the monitoring device. In certain implementations, the configuration server can delay transmission of the encoded key until it has received confirmation that the monitoring device has been activated.

As noted above, master and local versions of lookup tables can be used to transmit setting and threshold information to a monitoring device. In certain implementations, both the configuration server and the monitoring device have versions of the lookup tables with identical threshold information. Thus, by transmitting appropriate coordinate or lookup information from the master lookup table (i.e., the lookup table maintained by the configuration server) to the monitoring device, the monitoring device can identify the threshold and settings information from its local lookup table using the coordinate and lookup information. Additional information related to the lookup tables, as well as configuration of the monitoring device using the encoded key as received from the configuration server, is described below in reference to FIGS. 6-8.

FIG. 6 illustrates a sample master lookup table 600. As shown in FIG. 6, the master lookup table 600 includes values for two specific heartrate variables. In this example, Bradycardia onset values are listed in the far most left column. The values can be determined by, for example, the manufacturer to cover a range of values that are most likely to be selected by a majority of prescribing doctors. For example, as shown in FIG. 6, the Bradycardia threshold values range from 20-40 in increments of 2. Additionally, as shown in FIG. 6, Tachycardia onset values can be listed in the top row. The values can be determined by, for example, the manufacturer to cover a range of values that are most likely to be selected by a majority of prescribing doctors. For example, as shown in FIG. 6, the Tachycardia threshold values range from 150-200 in increments of 5.

Each row and column in the master lookup table 600 can also have an associated identifier. For example, as shown in FIG. 6, the row and column identifiers can range from 1-11. Thus, each individual combination of values for Bradycardia and Tachycardia can have an associated identifier pair (row, column). For example, if a doctor selects a Bradycardia onset threshold of 30, and a Tachycardia onset value of 175, the associated identifier pair is (6, 6), as indicated by the X on the master lookup table 600. In another example, a Bradycardia onset value of 26 and a Tachycardia onset value of 160 would have an identifier pair of (4, 3).

In the process as shown in FIG. 5, if the doctor prescribes a Bradycardia onset threshold of 30, and a Tachycardia onset threshold of 175, the configuration server would identify the database coordinates as (6,6). This location information would be used as the character string when encrypting and encoding the associated key for transmission to the monitoring device.

Additionally, in certain implementations, as the capabilities of the monitoring device increases, the master lookup table can be updated accordingly. When the master lookup table is updated, updated copies of local lookup tables can be distributed to all appropriate monitoring devices such that they have local copies of the updated information.

It should also be noted that, the master lookup table 600 as shown in FIG. 6, is organized as shown by way of example only. In certain implementations, the table can be organized such that the most commonly used threshold pairs are prioritized and moved to a higher position in the table, which the least commonly used threshold pairs are moved to a lower position in the table. Thus, when the configuration server is scanning the database for a selected pair (as selected by the doctor), commonly selected pairs will be identified more quickly than the less common pairs.

Figure 7:
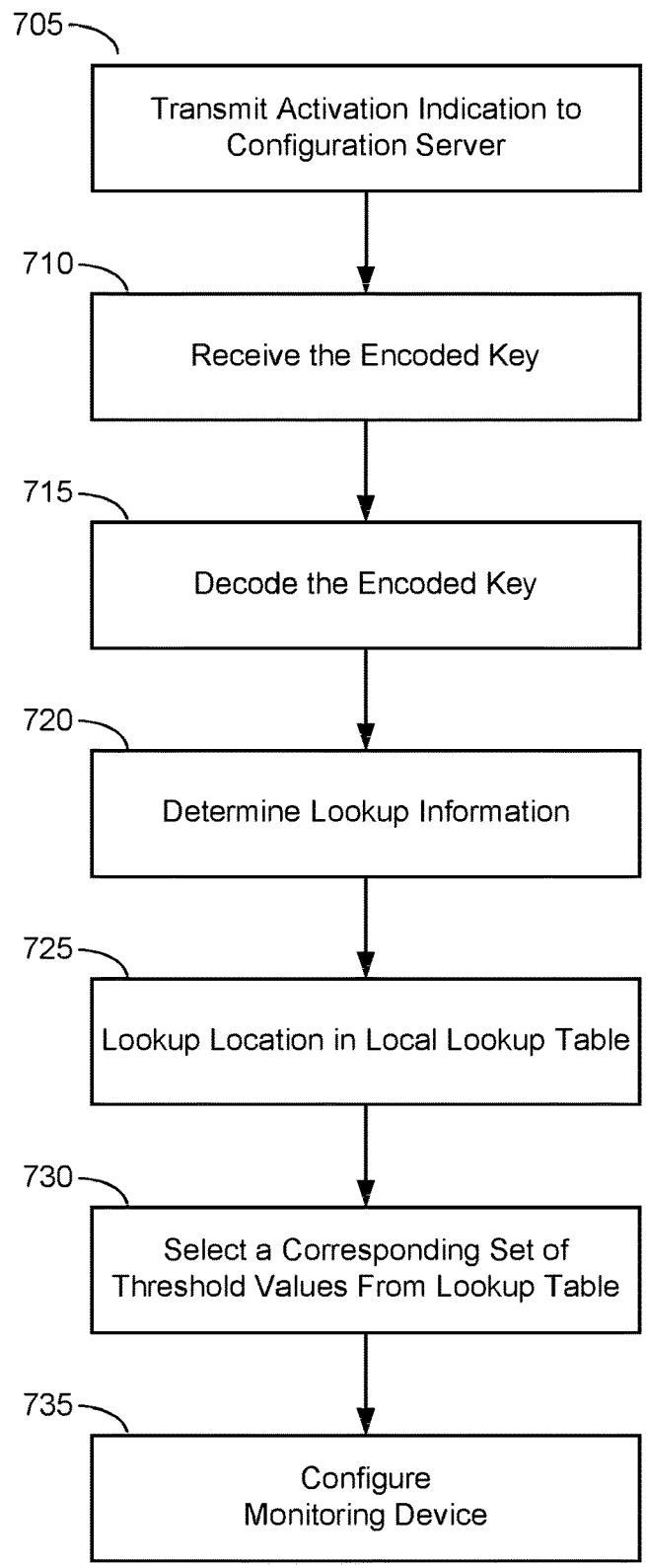
FIG. 7 illustrates a sample process flow for configuring a wearable medical device, in accordance with an example of the present disclosure.

FIG. 7 illustrates a sample process as implemented by a monitoring device such as monitoring device 404 as described above in relation to FIG. 4. The monitoring device can transmit 705 an activation indication to the configuration server. For example, upon powering on, the monitoring device can be configured to operably connect to a network (e.g., via a wired connection or a wireless connection to, for example, a Wi-Fi network or a cellular data network) and transmit 705 a notification to the configuration server. The configuration server can then transmit updated configuration information to the monitoring device. Such an operation can be implemented, in certain implementations, as either a push or pull action. For example, the configuration server can be configured to, upon receiving the activation notification, immediately push updated configuration information to the monitoring device. In another example, the monitoring device can be configured to monitor a unique location for any updated information, and extract the updated information in a pull action. For example, each individual monitoring device can have a unique IP address encoded therein, the unique IP address directed to a data storage location specific to that monitoring device on, for example, the configuration server. The configuration server can be configured to store updated configuration information for that monitoring device at that IP address. The monitoring device can then be configured to regularly (e.g., every 5 minutes) check the unique IP address for any updated information and pull any updated information from that address.

The monitoring device can receive 710 the encoded key, through either a push or pull process as described above. As noted above, in certain implementations, the encoded key can include the encrypted string (including the location information of the threshold information as stored in the lookup tables) and the sealed session key (for decrypting the encrypted string).

In certain implementations, depending upon the amount of data to be transmitted to the monitoring device, the encoded key can be transmitted to the monitoring device using other communication protocols. For example, the configuration server can be configured to transmit the encoded key to the monitoring device using a short message service such as a cellular text message. The configuration server can include additional functionality to encrypt or otherwise encode the text message such that any device receiving the text message in error cannot determine what was included in the message. Similarly, the monitoring device can include additional functionality to decrypt or otherwise decode the text message, from which the encoded key can be extracted or identified.

Referring again to FIG. 7, the monitoring device can then decode 715 the encrypted key. As noted above, the key can be encrypted using a private/public key encryption scheme. Similarly, the encoded key can be decoded using standard private/public key encryption techniques. For example, a sample pseudo-code snippet for such a process can be:

```
Decode Received Encoded Key
    Get Private Key (locally stored)
    Create Asymmetric Cipher
    Initialize Cipher for Decryption Using Private Key
    Unseal Session Key Using Asymmetric Cipher
    Create Symmetric Cipher
    Initialize Symmetric Cipher Using Session Key
    Decrypt Encrypted String (to get location information)
```

Based upon the decrypted string, including the location information for identifying the threshold values in a local lookup table, the monitoring device can determine 720 the lookup information (e.g., a row, column pair). The monitoring device can then look up 725 the location in the local lookup table (which is described in greater detail below in reference to FIG. 8). The monitoring device can then select 730 a corresponding set of threshold values from the lookup table as identified at the location defined by the location information. For example, a sample pseudo-code snippet for such a process can be:

```
At (coordinate):
    Load Threshold Information (X, Y)
        Tachycardia Threshold = X
        Bradycardia Threshold = Y
```

The monitoring device can then be configured 735 according to the selected set of threshold values. For example, the processor of the monitoring device can update a local configuration file based upon the loaded threshold information. After updating the local configuration file, the monitoring device can reboot or restart the monitoring process according to the updated threshold values. For example, a sample pseudo-code snippet for such a process can be:

```
In Configuration File:
    Update Operating Tachycardia Threshold
    Update Operating Bradycardia Threshold
    Save Updated Configuration File
    Operate Per Updated Configuration File
```

In certain implementations, the monitoring device can maintain or save a default configuration file. In the event that an updated configuration file causes an error or is otherwise corrupted, the monitoring device can revert to the default configuration file to maintain operation. The monitoring device can then attempt to update the configuration file again.

FIG. 8 illustrates a local lookup table 800 stored, for example, on monitoring device 404 as described above. As shown in FIG. 8, the local lookup table 800 includes values for two specific heartrate variables. In this example, Tachycardia and Bradycardia onset value pairs are listed in each individual cell in the table 800. Each row and column in the local lookup table 600 also has an associated identifier. For example, as shown in FIG. 8, the row and column identifiers can range from 1-11. Thus, each individual pair of values for Bradycardia and Tachycardia can have an associated identifier pair (row, column). For example, a Tachycardia onset value of 185 and a Bradycardia onset value of 28 would have the identifier (5, 8).

In the process as shown in FIG. 7, if the monitoring device decodes the encrypted key information to be database coordinates as (6, 6), the monitoring device can identify the threshold pair contained at the location in the local lookup table 800. In this example, the threshold pair would be a Tachycardia onset value of 175, and a Bradycardia onset value of 30.

In a specific example of the processes as described above in FIGS. 5-8, a patient can visit their doctor for a yearly evaluation including a cardiac exam. During the exam, the doctor may decide that they want to prescribe the patient a wearable cardiac monitoring device. If the doctor has the device in their office, the doctor can immediately configure and provide the device to the patient. For example, as noted above, the doctor can access an e-ordering or prescription application and identify the patient and device being prescribed to the patient. The application can prompt the doctor to enter threshold values for one or more arrhythmia settings on the medical device. For example, the doctor can be prompted to enter onset threshold values for both Bradycardia and Tachycardia. The doctor can enter those values and submit the information.

The application can transmit the threshold values to a remote configuration server for further processing. The remote configuration server can access a master lookup table and identify location information (e.g., an identifier pair) that corresponds to the doctor selected threshold information.

Manufacturer Configuration of a Wearable Medical Device

In certain examples, a doctor prescribing a monitoring device to a patient may not have the device in their office for providing to the patient. Rather, the doctor may order a device for delivery to the patient. However, in this scenario, the doctor may still want to provide customized threshold settings for the patient.

Figure 9:
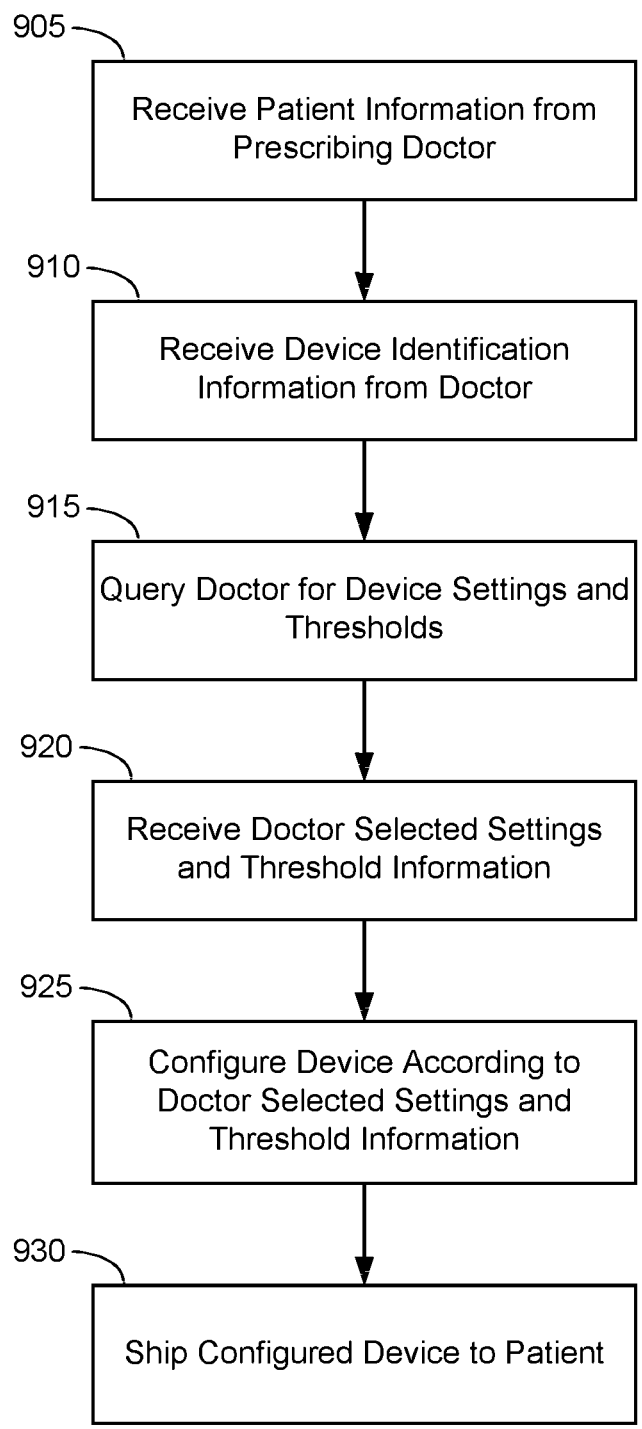
FIG. 9 illustrates a sample process flow for configuring a wearable medical device by a manufacturer or distributor, in accordance with an example of the present disclosure.

FIG. 9 illustrates a sample process as implemented by a manufacturer and/or distributor of the monitoring device to provide a device with customized settings to the patient. For example, a configuration device can receive 905 patient information from the prescribing doctor, similar to the process as described above in reference to FIG. 5. For example, when using an e-ordering application (as described above), the application can prompt or query the doctor for the patient information. For example, the application can prompt the doctor to provide various information such as patient name, patient identification number (e.g., health insurance policy number), demographic information, health history information, and other related information that is available to the doctor or included in the patient's medical record. The application can transmit the information to the configuration server.

The application can also prompt or query the doctor for information specific to the monitoring device being prescribed. For example, the application can query the doctor device model information. The configuration server can receive 910 the device identification information and determine the device type being prescribed as well as the default settings for that device. The configuration server can then query 915 the doctor via the application for updated settings information. For example, the configuration server can determine, based upon the type of device being prescribed, what settings are customizable on the device. To continue the above example, the configuration server can determine that both the Bradycardia and Tachycardia onset threshold values are customizable. Thus, the configuration server can run a routine to identify the customizable settings and query the doctor for values for those settings via the application. In certain implementations, the application can automatically prepopulate entry fields (e.g., drop-down menus) with either the default values or with a doctor's preferred values.

Once the doctor has entered the customized threshold and settings information (or accepted the default values), the configuration server can receive 920 the doctor selected settings and threshold information. Based upon the doctor selected settings, the manufacturer can configure 925 the prescribed device according to the doctor's customized settings and ship 930 the configured device to the patient. The manufacturer can further monitor the device to determine when the device has been activated. Upon activation, the manufacturer can run a diagnostic test to confirm that the device is operating according to the customized settings when being worn by the patient.

Other Configuration Schemes and Data Structures

Figure 10:
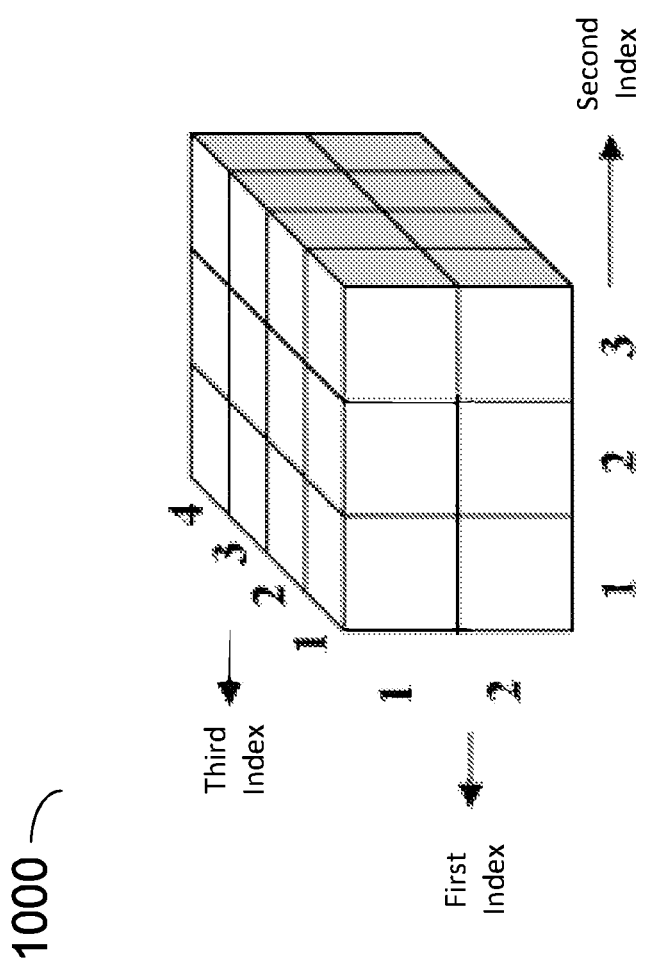
FIG. 10 illustrates s sample three-dimensional data structure for storing configuration information, in accordance with an example of the present disclosure.

It should be noted that the examples as shown above are provided for illustrative purposes only, and additional features, techniques, and processes can be implemented. For example, rather than the two-dimensional lookup tables as described above and shown in FIGS. 6 and 8, a three-dimensional data structure such as data structure 1000 as shown in FIG. 10 can be used. By using a three-dimensional data structure, an additional event or condition can be monitored, rather than two arrhythmia events as described above. For example, a heartrate change over time threshold can be set by the doctor for monitoring, in addition to onset of Bradycardia and Tachycardia. Thus, when determining lookup information, the configuration server can determine a set of three-dimensional coordinates (X, Y, Z position information). Thus, the three-dimensional coordinates can be used when encoding the key as described above, and master and local copies of the three-dimensional data structure can be stored on the configuration server (the master version) and the monitoring devices (the local version).

In certain implementations, rather than using master and local lookup tables, a monitoring device can be configured to include multiple configuration files, each of which includes a unique set of setting and threshold information. When configuring, the configuration server can determine which of the locally stored configuration files the monitoring device should use and transmit an identifier (e.g., a file name or extension) to the monitoring device. The processor of the monitoring device can, for example, update its booting routine or power on routine to include, for example, a pointer to the appropriate configurations file such that, upon booting or powering on, the monitoring device loads the proper configuration.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A system for configuring an ambulatory medical device, the system comprising:
    an ambulatory medical device configured to monitor at least one electrocardiogram (ECG) signal received from a patient for an occurrence of one or more cardiac events; and
    a remote computing device configured to
        receive a set of threshold values related to operation of the ambulatory medical device, the threshold values identifying one or more conditions indicative of the occurrence of the one or more cardiac events, wherein the set of threshold values is a first predetermined set of threshold values,
        store a master lookup table that comprises a first plurality of sets of threshold values, wherein the first plurality of sets of threshold values comprise at least the first predetermined set of threshold values,
        transmit a copy of the master lookup table to the ambulatory medical device,
        query the master lookup table to determine a lookup code that identifies a location of the received set of threshold values in the master lookup table,
        establish a communication link with the ambulatory medical device,
        receive an activation notification indicating that the ambulatory medical device has been activated,
        encode a key, the encoded key comprising the lookup code, and
        after receiving the activation notification, transmit the encoded key to the ambulatory medical device;
    wherein the ambulatory medical device is further configured to
        receive the copy of the master lookup table,
        save the received master lookup table as a local lookup table,
        send the activation notification to the remote computing device,
        receive the encoded key from the remote computing device,
        decode the encoded key to generate a decoded key that identifies the set of threshold values,
        select, with reference to the decoded key, a corresponding set of threshold values from the local lookup table, and
        configure the ambulatory medical device to operate according to the corresponding set of threshold values selected from the local lookup table.

2. The system of claim 1, wherein the local lookup table comprises a second plurality of sets of threshold values, the second plurality of sets of threshold values comprising the first predetermined set of threshold values, wherein the corresponding set of threshold values is the first predetermined set of threshold values.

3. The system of claim 1, wherein operating according to the corresponding set of threshold values comprises monitoring the at least one ECG signal to determine whether one or more threshold values of the corresponding set of threshold values have been exceeded.

4. The system of claim 1, wherein the ambulatory medical device comprises a memory device implemented by a computer readable medium configured to store the local lookup table.

5. The system of claim 1, wherein selecting the corresponding set of threshold values comprises:
    determining a location in the local lookup table from the encoded key; and
    determining a set of threshold values stored in the local lookup table at the determined location.

6. The system of claim 1, wherein the remote computing device is further configured to
    query the ambulatory medical device to determine what set of threshold values the ambulatory medical device is operating according to; and
    confirm that the set of threshold values the ambulatory medical device is operating according to matches the received set of threshold values.

7. The system of claim 1, wherein the one or more cardiac events comprise at least one of: tachycardia, bradycardia, atrial fibrillation, atrio-ventricular block, Lown-Ganong-Levine syndrome, atrial flutter, sino-atrial node dysfunction, cerebral ischemia, syncope, atrial pause, or heart palpitations.

8. The system of claim 1, wherein the ambulatory medical device is configured to operate in both a therapeutic mode and a monitoring mode.

9. The system of claim 1, wherein the ambulatory medical device comprises at least one of a therapeutic medical device or a monitoring medical device.

10. The system of claim 9, wherein the ambulatory medical device comprises the therapeutic medical device, and wherein the therapeutic medical device comprises at least one of a wearable defibrillator or a cardiac pacing device.

11. The system of claim 9, wherein the ambulatory medical device comprises the monitoring medical device, and wherein the monitoring medical device is portable.

12. The system of claim 9, wherein the ambulatory medical device comprises the monitoring medical device, and wherein the monitoring medical device comprises at least three adhesive cardiac sensing electrodes configured to be disposed around the patient's torso.

13. The system of claim 9, wherein the ambulatory medical device comprises the monitoring medical device, and wherein the monitoring medical device comprises a motion sensor configured to track movement of the patient.

14. The system of claim 1, wherein the ambulatory medical device is configured to be worn by the patient for an extended period of time.

15. The system of claim 14, wherein the extended period of time comprises at least one of: a week, 30 days, one month, two months, three months, six months, or a year.

16. The system of claim 1, wherein the remote computing device is further configured to
    determine customizable settings for the ambulatory medical device, the customizable settings comprising at least a threshold value identifying an onset of at least one of the one or more cardiac events;
    query a caregiver for values for the customizable settings; and
    receive the values for the customizable settings from the caregiver;

wherein the received set of threshold values comprises the values for the customizable settings received from the caregiver.

17. A system for configuring an ambulatory medical device, the system comprising:
an ambulatory medical device configured to monitor at least one electrocardiogram (ECG) signal received from a patient for an occurrence of one or more cardiac events; and
a remote computing device configured to
receive a received set of threshold values related to operation of the ambulatory medical device, the received set of threshold values identifying one or more conditions indicative of the occurrence of the one or more cardiac events to be detected by the ambulatory medical device,
query a master lookup table to determine identification information associated with the received set of threshold values, wherein the master lookup table comprises a first plurality of sets of threshold values, wherein the received set of threshold values is included in the first plurality of sets of threshold values, and wherein the identification information identifies a location of the received set of threshold values from amongst the first plurality of sets of threshold values included in the master lookup table,
establish a communication link with the ambulatory medical device,
receive an activation notification indicating that the ambulatory medical device has been activated,
encode a key, the encoded key comprising the identification information associated with the received set of threshold values, and
after receiving the activation notification, transmit the encoded key to the ambulatory medical device.

18. The system of claim 17, wherein the ambulatory medical device is further configured to
receive the encoded key from the remote computing device;
decode the encoded key to generate a decoded key that identifies the received set of threshold values;
select, with reference to the decoded key, a corresponding set of threshold values from a local lookup table; and
configure the ambulatory medical device to operate according to the corresponding set of threshold values selected from the local lookup table.

19. The system of claim 18, wherein
the local lookup table comprises a second plurality of sets of threshold values,
the second plurality of sets of threshold values comprises the received set of threshold values, and
the corresponding set of threshold values is the received set of threshold values.

20. The system of claim 18, wherein operating according to the corresponding set of threshold values comprises monitoring the at least one ECG signal to determine whether one or more values in the corresponding set of threshold values have been exceeded.

21. The system of claim 18, wherein selecting the corresponding set of threshold values comprises:
determining a location in the local lookup table from the encoded key; and
determining a set of threshold values stored in the local lookup table at the determined location.

22. The system of claim 17, wherein the remote computing device is further configured to:
query the ambulatory medical device to determine an operating set of threshold values according to which the ambulatory medical device is operating; and
confirm that the operating set of threshold values matches the received set of threshold values.

23. The system of claim 17, wherein the remote computing device is further configured to:
determine customizable settings for the ambulatory medical device, the customizable settings comprising at least a threshold value identifying an onset of a particular cardiac event;
query a caregiver for values for the customizable settings; and
receive the values for the customizable settings from the caregiver;
wherein the received set of threshold values comprises the values for the customizable settings received from the caregiver.

24. The system of claim 17, wherein the identification information comprises row and column indices associated with the received set of threshold values in the master lookup table.

* * * * *